United States Patent [19]

Saksena et al.

[11] Patent Number: 4,788,190
[45] Date of Patent: Nov. 29, 1988

[54] 2,4,4-TRI- AND 2,2,4,4-TETRA SUBSTITUTED-1,3-DIOXOLANE ANTIFUNGAL, ANTIALLERGY COMPOUNDS

[75] Inventors: Anil K. Saksena, Upper Montclair; Alan B. Cooper, West Caldwell, both of N.J.; Henry Guzik, Brooklyn, N.Y.; Viyoor M. Girijavallabhan, Parsippany; Ashit K. Ganguly, Upper Montclair, both of N.J.

[73] Assignee: Schering Corporation, Kenilworth, N.J.

[21] Appl. No.: 946,352

[22] Filed: Dec. 24, 1986

[51] Int. Cl.[4] .................. A61K 31/54; A61K 31/395; C07D 405/04; C07D 249/08
[52] U.S. Cl. ................. 514/227.8; 514/255; 514/333; 514/340; 514/341; 514/342; 514/383; 514/397; 514/467; 514/235.8; 514/236.2; 544/366; 544/367; 544/3; 544/107; 544/113; 544/122; 544/364; 544/370; 546/256; 546/276; 546/277; 546/278; 548/124; 548/262; 548/336
[58] Field of Search ............... 544/366, 367, 3, 107, 544/113, 122, 364, 370; 546/256, 276, 277, 278; 548/124, 262, 336; 514/467, 222, 225, 237, 238, 240, 255, 333, 340, 341, 342, 383, 397

[56] References Cited

U.S. PATENT DOCUMENTS

| 3,575,999 | 4/1971 | Godefrol et al. | 260/309 |
| 3,936,470 | 2/1976 | Heeres et al. | 260/309 |
| 4,144,346 | 3/1979 | Heeres et al. | 548/366 X |
| 4,223,036 | 9/1980 | Heeres et al. | 548/262 X |
| 4,338,453 | 6/1982 | Gall | 548/263 |
| 4,456,605 | 6/1984 | Heeres et al. | 544/367 X |
| 4,490,530 | 12/1984 | Heeres et al. | 544/366 X |
| 4,577,020 | 3/1986 | Gall | 544/366 |
| 4,612,322 | 9/1986 | Ogata et al. | 548/262 X |
| 4,640,918 | 2/1987 | Kompis et al. | 548/262 X |
| 4,668,700 | 5/1987 | Krämer et al. | 514/467 |

FOREIGN PATENT DOCUMENTS 128383 6/1983 Japan .

OTHER PUBLICATIONS

Chem. Abst. 102 (25): 220882d. Jpn. Kokai Tokkyo Koho JP 59,212,491, Dec. 1, 1984.

Primary Examiner—Teddy S. Gron
Assistant Examiner—Virginia B. Caress
Attorney, Agent, or Firm—Thomas D. Hoffman; Gerald S. Rosen

[57] ABSTRACT

Novel 1,3-dioxolane compounds useful as antifungal and antiallergy agents and represented by the formula

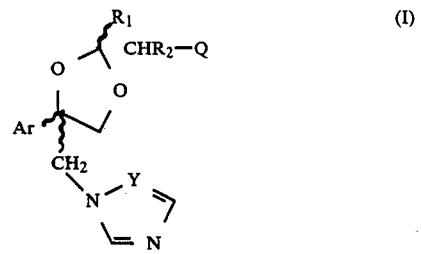

wherein Ar is thienyl, pyridyl, biphenyl, phenyl or phenyl substituted by one or more of halo, nitro, cyano, lower alkyl, lower alkoxy or perhalo(lower)alkyl; Y is CH or N;

Q is

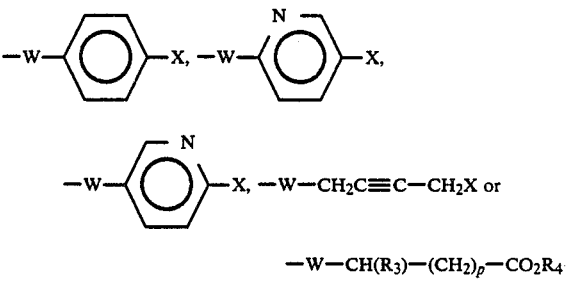

W is $-NR_5-$, $-O-$, $-S(O)_n-$;
X is $NO_2$, $NR_6R_7$ or $COR_8$;
$R_1$, $R_2$, $R_3$ and $R_4$ are independently hydrogen or lower alkyl; $R_5$ is hydrogen, lower alkyl or ($C_2$–$C_6$) alkanoyl; $R_6$ and $R_7$ are independently hydrogen, lower alkyl, phenyl or phenyl substituted by one or more of halo, perhalo loweralkyl, ($C_2$–$C_6$)alkanoyl lower alkyl, lower alkoxy or 2-loweralkyl-3-oxo-1,2,4-trirazol-4-yl or $R_6$ and $R_7$ taken together with the nitrogen atom in $NR_6R_7$ form substituted or unsubstituted heterocyclyl, said heterocyclyl substituents being ($C_2$–$C_6$)alkanoyl, lower alkyl, phenyl or phenyl substituted by one or more of halo, perhaloloweralkyl, ($C_2$–$C_6$)alkanoyl, loweralkyl, lower alkoxy or 2-loweralkyl-3-oxo-1,2,4-triazol-4-yl and $R_8$ is lower alkyl, lower alkoxy, $-NR_1R_2$, phenyl or phenyl substituted by one or more of halo, perhalo lower alkyl, lower alkyl, lower alkoxy, nitro, cyano or ($C_2$–$C_6$)alkanoyl and p is 0, 1, 2, 3, 4 or 5 and n is 0, 1, or 2 and the stereochemical isomers thereof in racemic or optically active form; or a pharmaceutically acceptable salt thereof.

20 Claims, No Drawings

＃ 2,4,4-TRI- AND 2,2,4,4-TETRA SUBSTITUTED-1,3-DIOXOLANE ANTIFUNGAL, ANTIALLERGY COMPOUNDS

BACKGROUND OF THE INVENTION

This invention relates to 2,4,4-tri- and 2,2,4,4-tetra substituted-1,3-dioxolane, e.g. (±) cis and (±)-trans-1-acetyl-4-[4-[[4-(2,4-dihalophenyl)-4-[1H-azol-1-yl($C_1$-$C_2$)alkyl]-1,3-dixolan-2-yl]alkoxy]phenyl] piperazine and related derivatives which exhibit antifungal and antiallergy activities, pharmaceutical composition thereof, methods of their use in treating or preventing susceptible fungal infections and in treating or preventing allergic reaction in a host including warmblooded animals such as humans.

This invention also relates to intermediates for preparation of the antifungal, antiallergic compounds.

U.S. Pat. Nos. 3,575,999, 3,936,470, 4,144,346 and 4,223,036 disclose 1,3-dioxolanes disubstituted at the 2-position by imidazol-1-ylmethyl or triazol-1-ylmethyl and phenyl or substituted phenyl and at the 4-position by hydrogen and substituted phenyloxymethyl.

Japanese Kokai No. 83-128,383 (published June 30, 1983) discloses 1,3-dioxolanes substituted at the 4-position by triazol-1-ylmethyl and by chloro substituted phenyl. The triazole compounds are useful as germicides, growth controlling agents and herbicides in the field of agriculture and horticulture.

None of the references disclose the compounds of the present invention.

SUMMARY OF THE INVENTION

The present invention provides a compound represented by the formula I

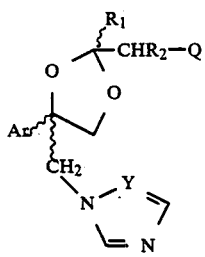

wherein Ar is thienyl, pyridyl, biphenyl, phenyl or phenyl substituted by one or more of halo, nitro, cyano, lower alkyl, lower alkoxy or perhalo lower alkyl;
Y is CH or N;
Q is

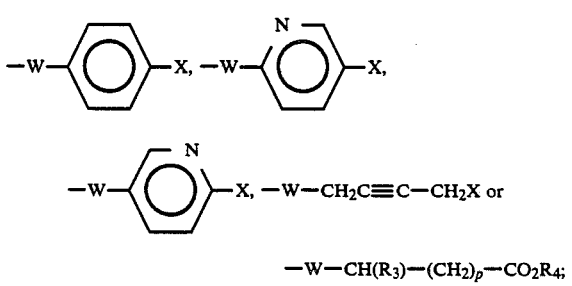

W is —$NR_5$—, —O— or —$S(O)_n$—;
X is $NO_2$, $NR_6R_7$ or $COR_8$;

$R_1$, $R_2$, $R_3$ and $R_4$ are independently hydrogen or lower alkyl; $R_5$ is hydrogen, lower alkyl or ($C_2$-$C_6$)alkanoyl; $R_6$ and $R_7$ are independently hydrogen, lower alkyl, phenyl or phenyl substituted by one or more of halo, perhalo lower alkyl, ($C_2$-$C_6$)alkanoyl, lower alkyl, lower alkoxy or 2-lower alkyl-oxo-1,2,4-triazol-4-yl or $R_6$ and $R_7$ taken together with the nitrogen in $NR_6R_7$ form substituted or unsubstituted heterocyclyl, said heterocyclyl substituents being ($C_2$-$C_8$)alkanoyl, lower alkyl, phenyl or phenyl substituted by one or more of halo, perhaloloweralkyl, ($C_2$-$C_6$)alkanoyl, lower alkyl, lower alkoxy, or 2-loweralkyl-3-oxo-1,2,4-triazol-4-yl; $R_8$ is lower alkyl, lower alkoxy, —$NR_1R_2$, phenyl or phenyl substituted by one or more of halo, perhalo lower alkyl, lower alkoxy, nitro, cyano, ($C_2$-$C_6$)alkanoyl; p is 0, 1, 2, 3, 4 or 5; n is 0, 1 or 2; and the stereochemically isomers thereof in racemic or optically active form; or a pharmaceutically acceptable salt thereof.

The present invention also provides a compound represented by formula II

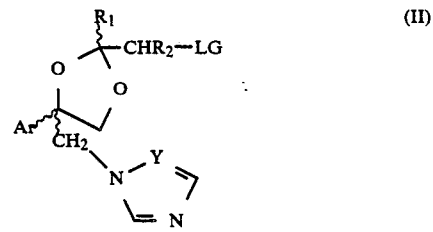

wherein Ar is thienyl, pyridyl, biphenyl, phenyl or phenyl substituted by one or more of halo, nitro, cyano, lower alkyl, lower alkoxy or perhalo lower alkyl;
Y is CH or N;
LG=a leaving group
$R_1$ and $R_2$ are independently hydrogen or lower alkyl;
and the stereochemical isomers thereof in racemic or optically active form.

The compounds represented by formula II are intermediates for the preparation of the compounds represented by formula I.

The compounds of formula I may be formulated into pharmaceutical compositions with a pharmaceutically acceptable carrier or diluent. The compounds of formula I may be used to treat mammals suffering from susceptible fungal infections, hyperproliferative skin disease (such as psoriasis), allergic reactions and/or inflammation by administering an effective amount for such purpose to the mammal.

The invention provides a composition for treating or preventing an allergic reaction in a host which comprises an antiallergically effective amount of a compound represented by the formula I and a pharmaceutically acceptable carrier or diluent.

The invention also provides a composition for treating or preventing susceptible fungal infection which comprises an antifungally effective amount of a compound represented by formula I and a pharmaceutically acceptable carrier or diluent.

The invention also provides a method of treating or preventing susceptible fungal infections which comprises administering to a host in need or such treating or preventing an antifungally effective amount of a compound of formula I or a pharmaceutical composition comprising such a compound and a pharmaceutically acceptable carrier or diluent.

The present invention still further provides a method of treating or preventing an allergic reaction in a host which comprises administering to such a host, e.g., warm-blooded animals including humans in need of such treatment or prevention, an antiallergically effective amount of a compound represented by formula I, or a pharmaceutical composition thereof.

DETAILED DESCRIPTION OF THE INVENTION AND THE PREFERRED EMBODIMENTS

As used in the specification and claims, the term "halogen" means bromine, chlorine or fluorine with chlorine and fluorine being preferred; fluorine is most preferred. The term "lower alkyl" refers to straight and branched chain hydrocarbon groups of 1 to 6 carbon atoms, such as methyl, ethyl, n-, and iso-propyl, n-, sec- and tert-butyl, n-, sec-, iso-, tert- and neo-pentyl, n-, sec-, iso- and tert-hexyl. The term "perhaloloweralkyl" refers to "lower alkyl" groups having only halogen substituents, e.g., —CCl$_2$—CF$_3$, —CF$_2$—Cl$_3$ as well as perhalo groups such as —CF$_2$—CF$_3$ or —CF$_3$; trifluoromethyl is preferred. The term "(C$_2$–C$_8$)alkanoyl" refers to straight and branched chain alkanoyl groups having 2 to 8 carbon atoms such as acetyl, propanoyl, butanoyl, 2-methylpropanoyl, 3-methylpropanoyl, pentanoyl, 2-methylbutanoyl, 3-methylbutanoyl, 4-methylbutanoyl, hexanoyl, 2-methylpentanoyl, 3-methylpentanoyl, 4-methylpentanoyl, 5-methylpentanoyl, heptanoyl, 3-methylheptanoyl, otanoyl, 2-ethylhexanoyl and the like. Acetyl is preferred.

The term "lower alkoxy" means a lower alkyl moiety univalently bonded to divalent oxygen, —O— and includes methoxy, ethoxy, n- and iso-propoxy, n-, sec- and tert-butoxy.

The term "2-lower alkyl-3-oxo-1,2,4-triazol-4-yl" means a moiety represented by the formula

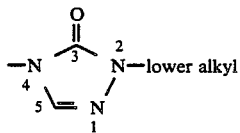

wherein "lower alkyl" is as defined hereinabove.

The term "heterocyclyl" refers to five and six-membered ring systems containing at least one carbon and one to four heteroatoms chosen from N, O and S, SO and SO$_2$. Typical suitable heterocyclyls include morpholino, thiomorpholino, 4-oxothiomerpholino, 4,4dioxothiomorpholino piperazino, pyrrolidino, piperidino, imidazolyl, 1,2,4-triazolyl, furanyl, thienyl, thiadiazolyls, especially 1,2,3-thiadiazol-4-yl, and 1,2,3-thiadiazol-5-yl, thiomorpholino, and pyridyls. The heterocyclyl may be attached via a carbon atom, e.g., N-methylpiperidin-4-yl, N-methylmorpholin-2-yl or via the nitrogen atom, e.g., piperidin-1-yl (commonly called piperidino), morpholin-4-yl (commonly called morpholino), N-methylpiperazin-4-yl (commonly called N-methylpiperazino), 1H-1-imidazol-1-yl or 4H-1,2,4-triazol-4-yl. 1H-1-imidazol-1-yl, 4H-1,2,4-triazol-4-yl and piperazino are the preferred heterocyclyls.

Substituted heterocyclyls include lower alkyl heterocyclyls especially N-loweralkylheterocyclyls such as N-methylmorpholin-4-yl, N-ethylpiperazino, N-(1-methylethyl)piperazino, but also 2-methylpyrrolidino, 4-methylpiperidino, 5-methyl-1H-1,2,4-triazol-3-yl, 3-methyl-1-phenyl-1H-1,2,4-triazol-5-yl, and 2-methylpyridyl; (C$_2$–C$_8$)alkanoyl heterocyclyls such as 2-acetylthiophenyl, 2-acetylpyrrolidino; haloheterocyclys such as 2-halo-3-thienyl, 2,5-dihalo-3-thienyl, and 5-halo-2-thienyl; N-(C$_2$–C$_8$)alkanoyl heterocyclyls such as N-acetylpiperazino and 4-acetylpiperidino; and aryl substituted heterocyclyls include heterocyclyls substituted by phenyl or substituted phenyl as defined herein such as N-phenylpiperazino, N-(4-chlorophenyl)piperazino, 2-(4-trifluoromethylphenyl)piperazino, and N-(p-toluyl)piperazino, N-(4-methoxyphenyl)piperazino. Piperazino is the preferred substituted heterocyclyl.

As used herein, the term "leaving group" (LG) means leaving groups readily removable under conventional conditions well known to those skilled in the organic synthetic arts so as to form the compound represented by formula I. Typical suitable leaving groups include halide especially bromide but also iodide, trifluoromethylsulfonyloxy, and 4-methylphenylsulfonyloxy.

Compounds of the present invention represented by formula I can exist in two isomeric forms, cis and trans. With reference to formulas I and II "cis" means Ar and R$_1$ are on the same side of the plane defined by the 1,3-dioxolane moiety. For example, 1-[4-[[4-(2,4-difluorophenyl)-4-(1H-1,2,4-triazol-1-ylmethyl)-1,3-dioxolan-2-yl]methoxy]phenyl]-4-(1-methylethyl)piperazine exists in the cis-2,4 and trans-2,4 forms as indicated by the formulas hereinbelow

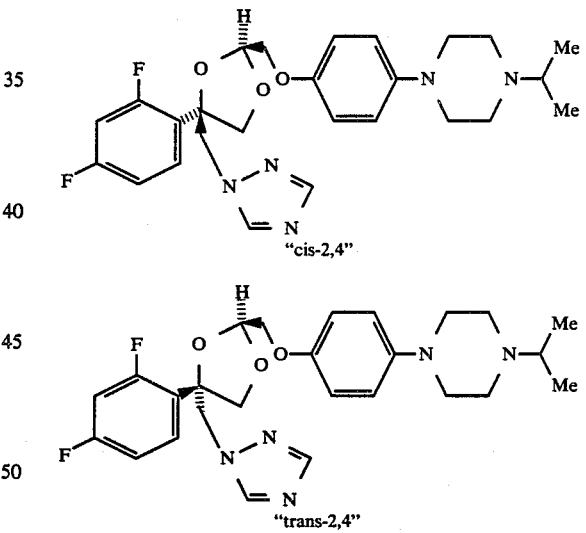

In the formula labelled "cis-2,4" the hydrogen and 2,4-difluorophenyl groups are both positioned on the same side or face or plane (below) of the formula. In the "trans-2,4" formula, the groups are positioned on opposite faces of the formula. Both forms are considered within the scope of this invention as are individual optical isomers e.g., (+)-cis-2,4 and (−)-cis-2,4, each of which can be obtained by resolution of a racemic mixture [(±)-cis-2,4] by conventional means well known to those skilled in the art. Compounds of formula II may also be resolvable, i.e., exists as individual optical isomers or mixtures thereof.

The compounds of represented by formula I exhibit broad spectrum antifungal activity, in conventional antifungal screening tests, against human and animal pathogens, such as the following: Aspergillus, Candida, Epidemophyton, Geotrichum, Monosporium, Rhodotorula, Saccharomyces, Torulopsis and Trichophyton.

The compounds of formula I exhibit topical and oral fungal activity in in vivo tests in animals that is comparable to that for ketoconazole, a commercial product.

The present invention also provides a composition for treating or preventing fungal infections comprising an antifungally effective amount of a compound represented by formula I or a pharmaceutically acceptable salt thereof and a pharmaceutically acceptable carrier or diluent.

The preferred pharmaceutically acceptable salts are nontoxic acid addition salts formed by adding to the compounds of the present invention about a stoichiometric amount of a mineral acid, such as HCl, HBr, $H_2SO_4$ or $H_3PO_4$, or of an organic acid, such as acetic, propionic, valeric, oleic, palmitic, stearic, lauric, benzoic, lactic, para-toluene sulfonic, methane sulfonic, citric, maleic, fumaric, succinic and the like.

The pharmaceutical compositions of the present invention may be adapted for oral, parenteral, topical or vaginal administration. They are formulated by combining the compound of formula I or an equivalent amount of a pharmaceutically acceptable salt thereof with any suitable, inert, pharmaceutically acceptable carrier or diluent.

Examples of suitable compositions include solid or liquid compositions for oral administration such as tablets, capsules, pills, powders, granules, solutions, suppositories, suspensions or emulsions. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration. They may also be manufactured in the form of sterile solid compositions which can be dissolved in sterile water, physiological saline or some other sterile injectable medium immediately before use.

Topical dosage forms may be prepared according to procedures well known in the art, and may contain a variety of ingredients, excipients and additives. The formulations for topial use include ointments, creams, lotions, powders, aerosols, pessaries and sprays. Of these, ointments, lotions and creams may contain water, oils, fats, waxes, polyesters, alcohols, or polyols, plus such other ingredients as fragrances, emulsifiers and preservatives.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use. Similarly, aerosol or non-aerosol sprays may be prepared using solutions or suspensions in appropriate solvents, e.g., difluorodichloromethane, for aerosols.

Parenteral forms to be injected intravenously, intramuscularly, or subcutaneously are usually in the form of a sterile solution, and may contain salts or glucose to make the solution isotonic.

The topical dosage for humans for antifungal use in the form of a pharmaceutical formulation comprising a compound of formula I (usually in the concentration in the range from about 0.5% to about 20% preferably from about 1% to about 10% by weight) together with a non-toxic, pharmaceutically accentable topical carrier, is applied several times daily to the affected skin until the condition has improved.

In general, the oral dosage for humans for antifungal use ranges from about 1 mg per kilogram of body weight to about 50 mg per kilogram of body weight per day, in single or divided doses, with about 2 mg per kilogram of body weight to about 20 mg per kilogram of body weight per day being preferred.

In general, the parenteral dosage for humans for antifungal use ranges for about 0.5 mg per kilogram of body weight per day to about 20 mg per kilogram of body weight per day, in single or divided doses, with about 10 mg per kilogram of body weight per day being preferred.

The compounds of this invention also are useful in treating or preventing an allergic reaction and/or inflammation in a host e.g. a warm blooded mammal such as man.

The pharmaceutical compositions useful for treating or preventinq allergic reactions and/or inflammation are analogous to those described hereinabove in reference to the antifungal pharmaceutical composition.

The compounds of formula I are effective non-adrenergic, non-antichlolinergic, anti-anaphylactic agents. The compounds may be administered by any convenient mode of administration for treatment of allergic reactions employing an antiallergically, or antiinflammatory effective amount of a compound of formula I for such mode.

In general, the oral dosage for human for antiallergy and/or antiinflammatory use ranges from about 10 mg to about 500 mg per kilogram of body weight per day, in single or divided doses. Preferably the total dosages are administered in 2-4 divided doses per day.

In general, the parenteral e.g. intravenous dosage for humans for antiallergy and/or antiinflammatory use ranges for about 0.1 mg per day to about 10 mg per kilogram of body weight per day, in single or divided doses.

The compounds of formula I may be administered by inhalation (aerosol or nebulizer). In general, the inhalation dosage for humans for antiallergy use ranges from about 0.1 to 5 mg per puff, one to four puffs may be taken every 4 hours.

When administered for the treatment of hyperproliferative skin disease, e.g. psoriasis, a compound of formula I may be administered topically, orally, rectally or oarenterally. When administered topically, the amount of compound administered varies widely with the amount of skin being treated, as well as with the concentration of active ingredient applied to the affected area. When administered orally, the compounds of formula I are effective for the treatment of hyperproliferative skin disease at daily doses ranging from about 0.1 mg/kg of body weight to about 500 mg/kg of body weight, preferably in 10 mg to 100 mg/kg of body weight, which may be administered in single or divided doses. When administered rectally, the compounds of formula I may be administered in doses ranging from about 0.1 mg to about 1000 mg. When administered parenterally, the compounds of formula I are effective for the treatment of hyperproliferative skin disease in daily doses ranging from about 0.1 mg/kg body weight to about 10 mg/kg body weight which may be administered in single or divided doses.

Included within the invention are preparations for tonical application to the skin whereby the compounds having structural formula I are effective in the treatment and control of skin diseases characterized by rapid rates of cell proliferation and/or abnormal cell proliferation, e.g., psoriasis.

In a preferred method of treating hyperproliferative skin diseases, a pharmaceutical formulation comprising a compound of formula I, (usually in concentrations in the range of from about 0.01 percent to about 10 percent, preferably from about 1 percent to about 5 percent) together with a non-toxic, pharmaceutically acceptable topical carrier, is applied several times daily to the affected skin until the condition has improved. Topical applications may then be continued at less frequent intervals (e.g. once a day) to control mitosis in order to prevent return of severe disease conditions.

It will be appreciated that the actual preferred dosages of the compounds of the present invention of formula I or pharmaceutically acceptable salts thereof will vary according to the particular composition formulated, the mode of application and the particular situs, host, the allergic reaction or disease being treated. Many factors that modify the action of the drug will be taken into account by the attending clinician, e.g., age, body weight, sex, diet, time of administration, rate of excretion, condition of the host, drug combinations, reaction sensitivities and severity of the disease or symptoms of the allergic and/or inflammatory reaction. Administration can be carried out continuously or periodically within the maximum tolerate dose. Optimal application rates for a given set of conditions can be readily ascertained by the attending clinician using conventional dosage determination tests.

As a result of the administration of a compound of formula I, a remission of the symptoms of the psoriatic patient, in most cases, can be expected. Thus, one affected by psoriasis can expect a decrease in scaling, erythema, size of the plaques, pruritus and other symptoms associated with psoriasis. The dosage of medicament and the length of time required for successfully treating each individual psoriatic patient may vary, but those skilled in the art of medicine will be able to recognize these variations and adjust the course of therapy accordingly.

The anti-allergy property of the compounds of formula I is evaluated by measuring the inhibition of the release of the mediator SRS-A (slow reacting substance of anaphylaxis) from sensitized guinea pig lung fragments after antigen challenge. The test procedure utilized is described hereinbelow.

Measurement of SRS-A Release From Sensitized Guinea Pig Lungs (a) Sensitization of Animals The release of SRS-A and histamine was studied in lungs from actively sensitized guinea pigs. Male Harley guinea pigs (250-300 g, obtained from Charles River or Dutchland Farms) were sensitized with 5 mg ovalbumin injected intraperitoneally and 5 mg subcutaneously in 1 ml saline on day one, and 5 mg ovalbumin injected intraperitoneally on day four. The sensitized animals were used 3-4 weeks later.

(b) Release of SRS-A

Sensitized guinea piqs were killed by a blow to the head and the lungs removed and cleaned of visable connective tissue, trachea and large blood vessels. The lungs from individual animals were sliced into fragments approximatelv 1 mm in thickness using a McIlwain chopper and then washed with oxygenated Tyrode's buffer. Weighed aliquots (approximately 400 mg wet weight) of lung were transferred into vials containing 2 ml of fresh Tyrode's solution and incubated in the presence or absence of test compound 12 min at 37° C. followed by challenge of the tissue with 20 μg ovalbumin/ml (final concentration). After an additional 15 min incubation, the vials were cooled to 4° C. and 1.5 ml of clear supernatant media was removed and mixed with 6 ml of cold 100% ethanol. This mixture was thoroughly vortexed and kept at −15° C. for 30 min to allow precipitation of protein. The samples were then centrifuged at 1000 x g for 15 min at 2° C. and the clear supernatant fluid removed into polyethylene tubes and taken to dryness at 50° C. under a stream of $N_2$ gas. The samples were stored at −70° C. until assayed for SRS-A by bioassay or radioimmune assay.

The compounds of formula I inhibit the release of SRS-A from sensitized guinea pig lung fragments as measured using the test techniques described above.

The compounds of formula I inhibit 5-lipoxygenase activity, which inhibitory activity has been associated with anti-allergy and anti-inflammatory activity. The compounds of formula I are thus useful for the treatment of allergies, allergic chronic obstructive lung diseases, inflammation, arthritis, bursitis, tendonitis, gout and other inflammatory conditions. The 5-lipoxygenase inhibitory activity of the compounds of formula I may be demonstrated by the procedure described below:

5-Lipoxygenase and Cyclooxygenase Assays with Mc-9 Mast Cells

The IL-3-dependent murine mast cell clone, MC-9, was used to test the effects of compounds of formula I on cyclooxygenase and lipoxygenase activities. The MC-9 cell line was grown in suspension culture (0.4 to $1.2 \times 10^6$ cells/ml) in RPMI 1640 medium (Gibco) with 10% fetal bovine serum (Hyclone) and 2–5% conconavalin-A conditioned supernatant Musch et. al., Prostagandins, pp. 405–430, (1985). Cells were harvested, washed twice by centrifugation, and resuspended in a $Ca^{++}$-free HEPES buffer (25 mM HEPES, 125 mM NaCl, 2.5 mM KCl, 0.7 mM $MgCl_2$, 0.5 mM EGTA and 10 mM glucose at pH 7.4).

MC-9 cells (0.39 ml at $7.5 \times 10^6$ cells/ml) were preincubated with DMSO vehicle with or without test compound (1 µl) for 4 min then incubated 5 min with [$^{14}C$] arachidonic acid (Amersham, 59 Ci/mole) at a 9 µM final concentration and A23187 (Calbiochem) at a 1 µM final concentration added in 10 µl of water:ethanol (9:1). The reaction was stopped by addition of methanol (0.4 ml), and cellular debris was removed by centrifugation. Aliquots (250 µl) of the incubations were run on a Waters two pump HPLC system fitted with a Waters C18, 10µ $8 \times 100$ mm µ-Bondapak radial compression column and C18 "Guard Pak". The column was initially eluted at 3 ml/min with water:methanol:acetic acid (67:33:0.08) containing 1 mM EDTA adjusted to pH 6.0 with ammonium hydroxide (Pump A). At 4 min, a linear gradient to reach 100% methanol (Pump B) at 9 min was established. Between 13 and 14 min, methanol was exchanged for the initial eluting solvent and by 19 min the column had been reequilibrated for the next sample. The effluent was analyzed by a continuous flow radioactivity monitor (model ROMONA-D) interfaced with a Hewlett Packard Lab Automation System for quantitation of radioactive products. These were predominantly prostaglandin $D_2$ which eluted at 4 min ($PGD_2$), leukotriene $C_4$ ($LTC_4$) which eluted at 6 min, and 5-hydroxyeicosatetraenoic acid (5-HETE) which eluted at 11 min (Musch, et al. (1985) Prostagandins 29, 405–430).

The results with and without test compounds were used to calculate percent inhibition of $PGD_2$, $LTC_4$ and HETE production for compounds of formula I.

The compounds of formula I are useful in the treatment of hyperproliferative skin disease, e.g., psoriasis, in mammals, e.g., humans, which may be demonstrated by their 5-lipoxygenase inhibitory activity as discussed above or by the Arachidonic Acid Mouse Ear Test as described below.

Arachidonic Acid Mouse Ear Test, Materials and Methods

Charles River, female, CD, (SD) BR mice, 6 weeks old, are caged 8 animals/group and allowed to acclimate 1–3 weeks prior to use.

Arachidonic acid (AA) is dissolved in reagent grade acetone (2 mg/0.01 ml) and stored at −20° C. for a maximum of 1 week prior to use. Inflammatory reactions are induced by applying 10 ml of AA to both surfaces of one ear (4 gm total).

Test drugs are dissolved in either reagent grade acetone or aqueous ethanol (only if insoluble in acetone) at the same doses selected by Opas et al., Fed. Proc. 43, Abstract 2983, p. 1927 (1984) and Young et al., J. Invest. Dermatol. 82, pp. 367–371 (1984). These doses are employed to ensure maximum responses and to overcome any difference in topical absorption which could occur with any drug applied in an aqueous ethanol vehicle. The test drug is applied 30 minutes prior to challenge with AA.

The severity of the inflammation is measured as a function of increased ear weight. A 6 mm punch biopsy is removed 1 hour after AA challenge and weighed to the nearest 0.1 mg. Mean ± standard error and all possible comparisons are made via Duncans Multiple Range Statistic.

GENERAL SYNTHETIC PREPARATIONS

The compounds of the present invention represented by formulas I and II may be synthesized utilizing the sequence of reaction illustrated in the following Schemes 1, 2 and 3.

Scheme 1

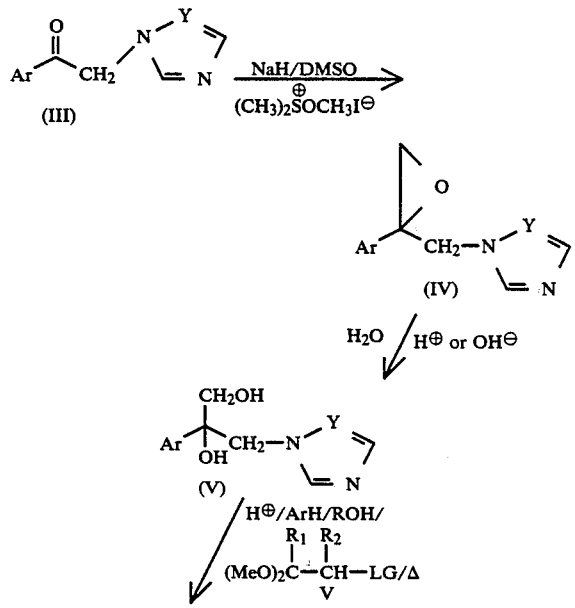

-continued
Scheme 1

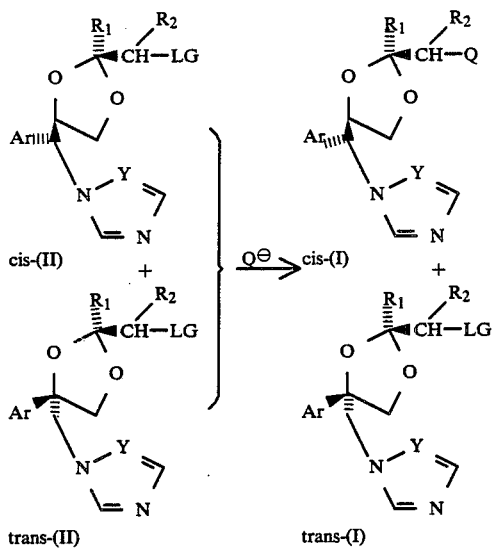

In the formulas listed in the Schemes, Ar, Y, $R_1$, $R_2$ LG and Q have exactly the same meaning as defined hereinabove.

Compound III may be treated with dimethyloxosulfonium methylide [produced and used as described in "Reagents for Organic Synthesis" (Feiser and Feiser), Vol. 1, pages 314 to 316, J. Wiley and Sons, Inc. N.Y. (1967)] to produce the oxirane of formula IV. See for example Example 1 herein. Compounds of formula III are readily prepared by treating the corresponding readily available phenylacyl halides with the appropriate azole anion in aprotic solvents such as dimethylformamide (hereinafter "DMF"). The oxirane of formula IV may be treated with aqueous mineral acid or alkali metal hydroxide to produce the 1,3-propanediol of formula V. The intermediates of formula II may be prepared by treating the 1,3-propanediols with the dialkylacetal or dialkylketal of formula VI in the presence of an acid in an organic solvent. Typical suitable acids include mineral acids such as HCl, HBr, $H_2SO_4$ and sulfonic acids such as p-toluene sulfonic acid. Solvents that may be used include aromatic hydrocarbons (ArH) such as benzene and toluene, halogenated hydrocarbons including carbon tetrachloride, chloroform, methylene chloride and dichloroethane or mixed solvents such as aromatic hydrocarbons and lower alkanols (ROH) e.g. methanol, ethanol, propanol or butanol. Reflux temperatures and removal of water such as by use of a Dean-Stark trap facilitates the reaction. The aldehydes and ketones corresponding to formula VI may also be used in place of acetals and ketals VI in the reaction with V. The mixture of products cis-II and trans-II may be separated by, for example, conventional chromatographic techniques well known to synthetic organic chemists or may be reacted with the anions represented by O⊖, anions, such as

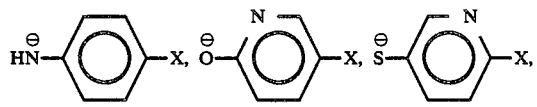

or ⊖O—$CH_2$—C≡C—$CH_2$—X which may be prepared from the corresponding acids by reaction with bases such as alkali metal hydride, e.g. NaH, or alkaline earth hydride, e.g. $CaH_2$ or alkali metal amides, e.g. $NaNH_2$, in aprotic solvents such as DMF. The reaction of O⊖ with cis-II/trans-II may be carried out in aprotic solvents such as DMF at room temperatures (20°–30° C.). The mixtures of cis-I and trans-I may be isolated and separated using standard separation techniques such as chromatography.

The compounds of formula I have at least two asymmetric carbon atoms in their structures, namely those located at the 2- and 4-positions of the dioxolane ring, and consequently can exist in different stereochemically isomeric forms. The stereochemically isomeric forms of I and the pharmaceutically acceptable acid addition salts thereof are intended to be within the scope of this invention.

The diastereomeric racemates of I, denoted as cis and trans forms respectively, according to the rules described in C.A., 76, Index Guide, Section IV, p. 85 (1972), may be obtained separately by conventional methods. Appropriate methods which may advantageously be employed therefore include, for example, selective crystallization and chromatography separation, e.g. column chromatography.

Since the stereochemical configuration is already fixed in the intermediates (II) it is also possible to separate cis and trans forms at this or even an earlier stage, whereupon the corresponding forms of (I) may be derived therefrom in the previously indicated manner. The separation of cis and trans forms of such intermediates may be performed by conventional methods as described hereinabove for the separation of cis and trans forms of the compounds (I).

It is evident that the cis and trans diastereomeric racemates may be further resolved into their optical isomers, cis(+), cis(−), trans(+), and trans (−) by the application of methodologies known to those skilled in the art.

Schemes 2 and 3 illustrate sequences of reaction useful for preparation of the 1,3-propane diols of formula V.

Scheme 2

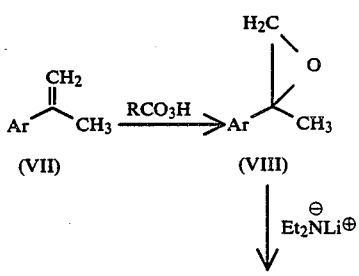

-continued
Scheme 2

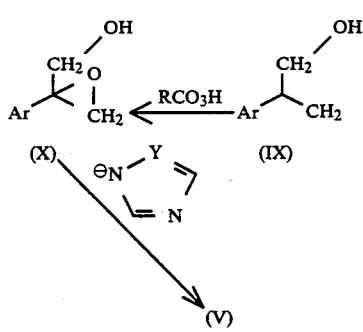

The readily available α-styrene compounds of formula VII may be treated with peracid (RCO₃H) to produce the oxirane of formula VIII. Peracids such as perchloroper-benzoic acid or peracetic acid may be used in halogenated solvents such as chloroform or methylene chloride. The oxirane VIII may be treated with hindered bases such as alkali metal di(loweralkyl)amides to produce the α-aryl-α-methylene ethanols of IX. Hindered bases such as alkali metal diloweralkylamides may be readily formed in situ by reaction of strong bases such as n-butyl lithium with the corresponding di(loweralkyl)amine. Reaction of IX with peracids produces the 1-hydroxymethyl-1-aryl oxiranes of X.

Treatment of the oxiranes X with azole anions in aprotic solvents such as DMF provides 1,3-propanediols of formula V.

Scheme 3 provides an alternative synthesis of 1,3-propanediols V starting from the methyl aryl ketones of formula XI which are readily available or may be prepared by methods well known to the skilled synthetic organic chemist.

Scheme 3

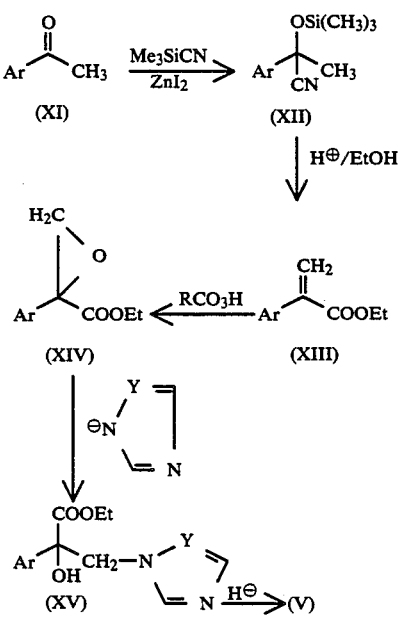

The aryl methyl ketone XI may be treated with trimethylsilylcyanide and zinc iodide at 50° C. to produce compounds of formula XII to prolonged acid-catalyzed alcoholysis to produce the ethyl α-aryl-α-methylacetate of formula XIII. Reaction of XIII with peracid provides the oxirane XIV which when treated with azole anion gives the ethyl α-aryl-α-hydroxypropanoate of formula XV. Hydride reduction of XV with, for example, LiAlH₄ in ether provides the 1,3-propane diols of formula V. The following Examples illustrate the preparation of compounds of this invention.

EXAMPLE 1

2-(4-CHLOROPHENYL)-3-(1H-1,2,4-TRIAZOL-1-YL)-1,2-PROPANEDIOL

To a stirred solution of p-chlorophenacyl-1H-1,2,4-triazole (10.3 g, 40 mmol) in 65 mL of toluene and 65 mL of 20% w/w NaOH at 60° C., add trimethylsulfoxonium iodide (8.84 g, 40 mmol) and cetrimide (0.39 g). Continue to stir the so-formed mixture at 60° C. for 1.5 h. Separate the toluene layer, add 20 mL of H₂O to the aqueous layer and extract with two 100 mL portions of ethyl acetate (EtOAc). Combine both the toluene and EtOAc layers, dry over MgSO₄, filter, and evaporate off the solvents. Add 100 mL of acetone, 6 mL of concentrated H₂SO₄, 20 mL of H₂O, and reflux for 3 hr. Evaporate the acetone at 45° C. under reduced pressure. Add 20 mL of sat. sodium bicarbonate and extract with two 100 mL portions of EtOAc. Wash the combined EtOAc layers with sat. brine, dry over MgSO₄, and evaporate the EtOAc to obtain a syrup. Chromatograph the syrup on 300 g of silica gel using 5% MeOH/CH₂Cl₂ as the eluent under flash chromatography conditions to obtain 3.63 g of the title product.

EXAMPLE 2

(±)CIS AND TRANS-1-[[2-(BROMOMETHYL)-4-(4-CHLOROPHENYL)-1,3-DIOXOLAN-4-YL]METHYL]-1H-1,2,4-TRIAZOLE

To a suspension of 2-(4-chlorophenyl)-3-(1H-1,2,4-triazol-1-yl)-1,2-propanediol of Example 1 (3 g, 0.012 mol) in 150 mL of dry toluene, add p-toluene sulfonic acid monohydrate (2.55 g, 0.013 mol), bromoacetaldehyde diethylacetal (2.25 mL, 0.015 mol), and reflux using a Dean-Stark trap. After 5 hr, cool to room temperature. Add EtOAc (100 mL) and wash with 100 mL of sat. NaHCO₃. Dry over MgSO₄, filter, and evaporate off the solvents to obtain 5.2 g of crude product. Chromatograph the diastereomeric mixture on 200 g of silica gel using 50% EtOAc/hexane as the eluent to obtain 1.52 g of cis-isomer followed by 2.42 of the trans-isomer of the title compound.

EXAMPLE 3

(±)CIS OR TRANS-1-ACETYL-4[4-[[4-(4-CHLORPHENYL)-4-(1H-1,2,4-TRIAZOL-1-YLMETHYL)-1,3-DIOXO-LAN-2-YL]METHOXY]PHENYL]PIPERAZINE

To a suspension of NaH (50%) dispersion (0.38 g, 8 mmol), in 30 mL of DMF, add 1-(4-hydroxyphenyl)-4-acetylpiperazine (1.76 g, 8 mmol). After stirring 1 hr at room temperature add, dropwise, the title compound of Example 2 (2.4 g, 6.7 mmol) in 10 mL of DMF. After stirring 18hr, add 50 mL of sat. brine and extract with two 100 mL portions of EtOAc. Dry the combined EtOAc layers over MgSO₄, filter, and evaporate off the solvents at 60° C. and reduced pressure. Chromatograph the resulting oil on 200 g of silica gel using 3%

MeOH/CH2Cl2 as the eluent, under flash chromatography conditions, to obtain 1.45g of the title compound.

EXAMPLE 4

PREPARATION OF 2-(4-CHLOROPHENYL)-3-(1H-1,2,4-TRIAZOL-1-YL)-1,2-PROPANEDIOL (a) 2-(4-CHLOROPHENYL)-2-METHYLOXIRANE

To a stirred and cooled solution (0°–5° C.) of 4-chloro-α-methylstyrene (15.2g) in chloroform (350 mL), add m-chloroperbenzoic acid (21.6 g). Stir the reaction mixture for 1 hr by which time all starting material will have reacted to give virtually a single product. Remove the m-chlorobenzoic acid formed by washing chloroform solution with aqueous NaHCO3 followed by water (150 mL). Dry the chloroform solution (Na2SO4) and evaporate to dryness to provide a colorless oil. Distill the oil in vacuo (1 mm) and collect fractions distilling between 65°–72° to give the title compound (8.8 g).

(b) β-(4-CHLOROPHENYL)-β-METHYLENE ETHANOL

To a cooled solution (5° C.) of diethylamine (3.2 g) in dry diethyl ether (100 mL) add (under N2 atmosphere) n-butyl lithium (29 mL, 1.55M solution in n-hexane). Maintain the temperature between 5° and 10° C. during the addition of n-butyl lithium. Add the epoxide of Example 4a, 2-(4-chlorophenyl)-2-methyloxirane, (5 g) via syringe as a solution in dry diethyl ether (25 mL). Allow the reaction mixture to warm to ambient temperature and then reflux for 3 hr. After cooling to 0°–5° C., add water (100 mL) carefully, separate the ether layer and wash with 1N HCl, water, and aqueous NaHCO3. Dry the ether layer (NaSO4), and evaporate the ether in vacuo, to give colourless oil (3.1 g). Chromatograph the oil on silica gel to provide the title compound.

(c) 2-(4-CHLOROPHENYL)-2-HYDROXYMETHYLOXIRANE

To a solution of the compound prepared in Example 4(c), β-(4-chlorophenyl)-β-methylene ethanol (1.05g) in chloroform (50 mL) add, with cooling, (ice bath) a solution of m-chloroperbenzoic acid (1.2g) in chloroform. Stir the chloroform solution for 4 hr. Wash the chloroform solution, successively, with aqueous 10% NaHSO3 (to remove excess per acid) followed by aqueous NaHCO3 and finally with water. Dry (Na2SO4) the chloroform solution. Remove the chloroform in vacuo to provide the title compound as a colourless oil (0.83 g). Use the title compound without any further purification in the next reaction.

(d) 2-(4-CHLOROPHENYL)-3-(1H-1,2,4-TRIAZOL-1-YL)-1,2-PRODANEDIOL

To a suspension of NaH (0.09 g) in dry DMF (20 mL), add 1,2,4-triazole (0.27 g), and stir the so-formed mixture for 1 hr. Add a solution of the epoxy alcohol prepared in Example 4(c), 2-(4-chlorophenyl)-2-hydroxymethyloxirane (0.8g) in dry DMF (15 mL). Heat the reaction mixture (bath temperature 70°–75°) for 2½ hours. Remove most of the DMF in vacuo and distribute the residue between water (60 mL) and chloroform (100 mL). Separate the chloroform layer, wash with water, dry over Na2SO4 and evaporate the solution to provide the title compound as a crystalline solid (0.7 g). This diol compound was identical in all respects to the product derived from acid hydrolysis of 1-[[2-(4-chlorophenyl)oxiranyl]methyl]-1H-1,2,4-triazole.

EXAMPLE 5

PREPARATION OF 2-(2,4-DICHLOROPHENYL-3-(1H-IMIDAZOL-1-YL)-1,2-PROPANEDIOL (a) 2,4-DICHLOROACETOPHENONE CYANOHYDRIN-O-TRIMETHYLSILYLETHER

Heat a mixture of 2,4-dichloroacetophenone (48.5 g) trimethylsilylcyanide (25.2 g) and zinc iodide (0.09 g) at 50° C. for 3 hours. Allow the reaction mixture to stand overnight at room temperature. Isolate the title compound as an oil and use it in the next reaction as such without further purification.

(b) ETHYL-α-(2,4-DICHLOROPHENYL)-α-METHYLENEACETATE and α-(2,4-DICHLOROPHENYL)-α-METHYLENEACETAMIDE Add the cyanohydrin prepared in Example 5(a), 2,4-dichloroacetophenone cyanohydrin-O-trimethylsilylether, (75 g) dropwise to a solution of concentrated H2SO4 containing 4% SO3 (60 mL) and 250 mg of copper powder at 40° C. During the addition, maintain the reaction temperature between 80°–85° C. (water bath). After all cyanohydrin is added, raise the temperature to 100° C. and heat the reaction mixture at this temperature for 30 min. Cool the reaction mixture to 90° C. and carefully treat with water (26 mL) and ethanol (60 mL). Heat the mixture at 100° C. for 15 hrs, cool and dilute with ice cold water (200 mL). Separate the organic layer, dilute with CH2Cl2 (100 mL) and wash with brine (100 mL). Extract the combined aqueous phase containing solids twice with EtOAc (400 mL), wash with saturated NaHCO3, water (100 mL each) and dry over Na2SO4. Evaporate EtOAc in vacuo to give an oil containing a crystalline solid. Dilute this residue with a small volume of CH2Cl2-separated crystals of α-(2,4-dichlorophenyl)-α-methyleneacetamide which were collected by filtration (26 g). Combine the filtrate with the organic layer obtained earlier and chromatograph the concentrate on silica gel (300 g) to provide ethyl-α-(2,4-dichlorophenyl)-α-methyleneacetate.

(c) ETHYL 2-(2,4-DICHLOROPHENYL)OXIRANECARBOXYLATE

Treat a stirred solution of the styrylester of Example 5(b), ethyl α-(2,4-dichlorophenyl)-α-methylene acetate, (20.6 g) in chloroform (500 mL) with m-chloroperbenzoic acid (16.5 g) and heat the mixture at reflux overnight. Cool the reaction mixture, treat with 10% aqeous sodium bisulfite solution to remove excess peracid, wash with aqueous NaHCO3, water and dry over Na2SO4. Evaporate CHCl3 in vacuo to give an oil. Chromatography the oil on silica gel to give the title compound (10.6 g) and unchanged styryl ester starting material.

(d) ETHYL α-(2,4-DICHLOROPHENYL)-α-HYDROXY-3-(1HIMIDAZOL-1-YL)-PROPANOATE

Treat a solution of the compound prepared in Example 5(c), i.e., ethyl 2-(2,4-dichlorophenyl) oxiranecarboxylate, (8 g) in dry DMF (100 mL) with imidazole (2.1 g) and heat the mixture (bath temp. 140°–150° C.) for 4 hr. Remove the DMF in vacuo. Take up the residue in water and extract with EtOAc. Dry EtOAc extract with Na$_2$SO$_4$ and evaporate to dryness to provide a crystalline residue. Recrystallize the residue from EtOAc-n-hexane to give 4.2 g of the title comoound, m.p. 177°–179° C.

(e) 2-(2,4-DICHLOROPHENYL)-3-(1H-IMIDAZOL-1-YL)-1,2-PROPANEDIOL

Add a solution of the hydroxy-ester of Example 5(d), i.e., ethyl 2-(2,4-dichlorophenyl)-2-hydroxy-3-(1H-imidazol-1-yl)-proanoate (4.1 g) in dry tetrahydrofuran (200 mL) dropwise, with stirring, to a suspension of LiAlH$_4$ (1.5g) in tetrahydrofuran (300 mL). Heat the reaction mixture at reflux for 18 hr and cool (ice bath). Carefully add EToAc to destroy excess LiAlH$_4$ and then add 10% Na-K-tartarate (50 mL). Evaporate most of the tetrahydrofuran in vacuo and extract the remaining aqueous suspension with EtOAc. Wash the EtOAc extract with saturated NaCl solution, dry Na$_2$SO$_4$ and evaporate to dryness to provide 4.2 g of a crystalline solid. Recrystallize the solid from EtOAc to yield the title compound, m.p. 146°–148° C.

EXAMPLE 6

2-(2,4-DICHLOROPHENYL)-3-(1H-1-IMIDAZOL-1-YL)-1,2-PROPANEDIOL

Heat a solution of 1-[[2-(2,4-dichlorophenyl) oxiranyl]methyl]-1H-imidazole (12g) [prenared in accordance with a procedure described in British patent application No. 2,078,719A, published 13 Jan. 1982] in 90% formic acid (250 mL) at reflux for 15hr. Eyaporate the reaction almost to dryness in vacuo, take up the residue in water (100 mL) and carefully basify with aqueous K$_2$CO$_3$. Add sufficient methanol (100 mL) to dissolve the contents, and heat the mixture (bath temp. 100° C.) for 1 hr. Eyaporate the solvents in vacuo and isolate the product by extraction with CHCl$_3$. Concentrate chloroform extract to provide colourless crystals of the title compound (10 g), m.p. 127°–128° C.

EXAMPLE 7

(±) CIS AND TRANS-1-[[2-(BROMOMETHYL)-4-(2,4-DICHLOROPHENYL)-1,3-DIOXOLAN-4-YL]METHYL]-1H-IMIDAZOLE

To a well stirred suspension of 2-(2,4-dichlorophenyl)-3-(1H-imidazol-1-yl)-1,2-propanediol prepared in Example 5 (4 g) in toluene (200 mL) and n-butanol (5 mL), add successively p-toluenesulfonic acid monohydrate (2.9 g) and bromoacetaldehyde diethylacetal (2.7 g). Heat the mixture gently at reflux and distill the ethanol (5 hr). Add additional toluene (100 mL) and heat the mixture at reflux gently overnight. Cool the reaction mixture, dilute with EtOAc (100 mL) and wash with aqueous NaHCO$_3$. Dry the organic phase with Na$_2$SO$_4$ and evaporate to dryness in vacuo to provide a gummy product. Chromatograph the gummy product on silica gel (200 g) using 20% n-hexane/EtOAc as eluent to give the cis-isomer (less polar) 1.38 g and the trans-isomer (more polar) 2.36 g of the title compounds.

EXAMPLE 8

(±)CIS-1-ACETYL-4-[4-[[4-(2,4-DICHLOROPHENYL)-4-(1H-IMIDAZOL-1-YLMETHYL)-1,3-DIOXOLAN-2-YL]METHOXY]PHENYL]PIPERAZINE

To a stirred suspension of NaH (60% dispersion in mineral oil, 0.196 g) in dry DMF (10 mL) under argon atmosphere, add 1-acetyl-4-(4-hydroxyphenyl)-piperazine (1.08 g). Heat the mixture (bath temp. 50° C.) for 1 hr until H$_2$ evolution has ceased. To the so formed sodium phenoxide, add the cis isomer prepared in Example 8 (1.28 g, dried by azeotropic distillation of a benzene solution) in dry DMF (2 mL). Heat the mixture (bath temp. 60°) with stirring for 20 hr. Cool, add water (10 mL) and extract the reaction product with EtOAc (4×50 mL). Wash the EtOAc extracts with water (10 mL) and dry with Na$_2$SO$_4$. Eyaporate the organic extract in vacuo to give the crude product as a brown gum. Chromatograph the brown gum on silica gel (100 g) using 1–10% methanol/chloroform as eluent to give the title compound as an amorphous solid (0.8968 g).

EXAMPLE 9

(±)TRANS-1-ACETYL-4-[4-[[4-(2,4-DICHLOROPHENYL)-4-(1H)-IMIDAZOL-1-YLMETHYL)-1,3-DIOXOLAN-2-YL]METHOXY]PHENYL]PIPERAZINE

Follow the procedure of Example 8, but add 1.4 g of (±)trans-1-[[2-(bromomethyl)-4-(2,4-dichlorophenyl)-1,3-dioxolan-4-yl]methyl]-1H-imidazole prepared in Example 8 to 1.24 g of 1-acetyl-4-(4-hydroxyphenyl) piperazine. Chromatograph on silica gel, to give 0.6 g of the title compound as an amorphous solid.

EXAMPLE 10

(±)CIS AND (±)-TRANS-1-[[2-(BROMOMETHYL)-4-(2,4-DICHLOROPHENYL)-2-METHYL-1,3-DIOXOLAN-4-YL]METHYL]-1H-IMIDAZOLE

To a well stirred suspension of 2-(2,4-dichlorophenyl)-3-(1H-imidazol-1-yl)-1,2-propanediol (3.4 g), in toluene (500 mL) and n-butanol (4 mL), add successively with p-toluenesulfonic acid monohydrate (2.47 g) and 2,2-dimethoxybromopropane (3.2 g). Heat the mixture gently at reflux for 36 hr. Treat the reaction mixture in a manner described in Example 7 to give a mixture of the title compounds. Chromatograph on silica gel to provide the title compound, cis-isomer (less polar) m.p. 145°–147° C., and trans-isomer (more polar) m.p. 128°–130° C.

EXAMPLE 11

(±)CIS-1-ACETYL-4[4-[[4-(2,4-DICHLOROPHENYL)-4-(1H-IMIDAZOL-1-YLMETHYL)-2-METHYL-1,3-DIOXOLAN-2-YL]METHOXY]-PHENYL]PIPERAZINE

To a stirred solution of 1-acetyl-4-(4-hydroxyphenyl)-piperazine (0.448 g) in DMF (5 mL) add NaH [(60%) dispersion; 0.085 g] under an argon atmosphere. Heat the mixture (bath temp. 50° C.) for 1 hr until H$_2$ evolution had ceased. Add successively (±)cis-1-[[2-(bromomethyl)-4-(2,4-dichlorophenyl)-2-methyl-1,3-dioxolan-4-yl]methyl]-1H-imidazole (0.5 g) prepared in Example 10 in one portion and a suspension of 18-crown-6-ether (0.326 g) in acetonitrile and heat the reaction (bath temp. 80° C.) for 5 days. Treat the reaction mixture in a manner described in Example 8 to give a crude solid. Chromatograph on silica gel to provide the title compound as an amorphous solid (0.36 g).

EXAMPLE 12

2-(2,4-DIFLUOROPHENYL)-3-(1H-1,2,4-TRIAZOL-1-YL)-1,2-PROPANEDIOL

Heat a solution of 1-[[2-(2,4-difluorophenyl)oxiranyl]methyl]-1H-1,2,4-triazole (57 g) [prepared as described in Example 2(c) of British patent application No. 2,099,818A, published 15 Dec. 1982] in formic acid (500 mL) at reflux overnight. Remove the solvent in vacuo at 85°. Dilute the residue with ice water (1 liter) and basify carefully with 10% $K_2CO_3$ solution. Dilute with MeOH (500 mL) and heat on steam bath (1.5hr). Remove the MeOH in vacuo and extract the remaining aqueous solution with EtOAc (2×500 mL). Wash the EtOAc layer with $H_2O$ and dry it over $MgSO_4$ and evaporate it to dryness to give 49.7 g of the title compound as a solid, m.p. 130°–132° C.

EXAMPLE 13

(±)CIS AND TRANS-1-[[2-(BROMOMETHYL)-4-(2,4-DIFLUOROPHENYL)-1,3-DIOXOLAN-4-YL]METHYL]-1H-1,2,4-TRIAZOLE

To a stirred suspension of 15 g of 2-(2,4-difluorophenyl)-3-(1H-1,2,4-triazol-1-yl)-1,2-propanediol prepared in Example 13 in toluene (600 mL), add successively with p-toluene sulfonic acid monohydrate (12.6 g) and bromoacetaldehyde diethyl acetal (14.7 cc) and heat the so-formed mixture at reflux overnight with azeotropic removal of water (Dean-Start trap). After 16 hr, cool and then wash the reaction mixture with sat. $NaHCO_3$ sol. (300 mL) and extract the aqueous phase with EtOAc (300 mL). Combine organic phases and wash them with $H_2O$ (200 mL). Dry with $Na_2SO_4$ and evaporate to dryness in vacuo. Chromatograph the residue on silica gel to obtain 3.9 g of the less polar cis isomer, m.p. 75°–77° C. and 7.2 g of the more polar trans isomer, m.p. 81°–84° C. of the title compound.

EXAMPLE 14

METHYL(±)CIS-6-[[[4-(2,4-DIFLUOROPHENYL)-4-(1H-1,2,4-TRIAZOL-1-YLMETHYL)-1,3-DIOXOLAN-2-YL]METHYL]THIO]HEXANOATE

Add sodium hydride 260 mg to a solution of methyl 5-mercapto-hexanoate 900 mg in dry DMF (50 mL) at room temperature. After ½ hour, add the less polar cis isomer (2.3 g) of Examples 13 in DMF (15 mL) and heat at 0° C. (bath temperature) for 2 h. Add the mixture to cold water (600 cc) and extract with EtOAc (400 mL). Wash the EtOAc layer with brine (200 mL), dry over $NaSO_4$ and evaporate to give an oil. Chromatograph the oil on silica gel to give 2.1 g of the title compound as an oil.

EXAMPLE 15

(±)CIS-6[[[4-(2,4-DIFLUOROPHENYL)-4-(1H-1,2,4-TRIAZOLE-1-YLMETHYL)1,3-DIOXOLAN-2-YL]METHYL]THIO]HEXANOIC ACID

Heat a solution of methyl (±)cis-6-[[[4-(2,4-difluorophenyl)-4-(1H-1,2,4-triazol-1-ylmethyl)-1,3-dioxolan-2-yl]methyl]thio]hexanoate prepared in Example 14 (100 mg) in Claisen alkali (5 mL) [Claisen, Ann., 418, page 96 (1919)] on a steam bath for ½ hour. Remove the methanol in vacuo, dilute the solution with water and acidify it carefully with conc. $H_2SO_4$. Filter the precipitate so-formed, wash with $H_2O$ and dry in a vacuum oven at 50° C. to provide a solid (75 mg). Recrystallize the solid from EtOAc:hexanes to give the title compound, m.p. 126°–129° C.

EXAMPLE 16

(±)CIS-1,1'-[4-(2,4-DIFLUOROPHENYL)-1,3-DIOXOLAN-2,4-DIYLBIS(METHYLENE)]BIS-[1H-1,2,4-TRIAZOLE]

Add sodium hydride (120 mg, 60% oil disp.) to a solution of triazole (210 mg) in dry DMF (10 mL) at room temperature and stir ½ hour. Add a solution of (900 mg) in DMF (10 mL) and heat the reaction for 1 hr at 80° C. Remove DMF in vacuo, take up the residue in water (50 mL) and extract with EtOAc (100 mL). Wash the EtOAc extract with brine (100 mL) dry over $Na_2SO_4$ and evaporate the solvent. Recrystallize the residue from EtOAc:hexanes to give 520 mg of the title compound as a solid, m.p. 168°–169° C.

EXAMPLE 17

(±)CIS-4-[4-[4-[4-[[4-(2,4-DIFLUOROPHENYL)-4-(1H-1,2,4-TRIAZOL-1-YLMETHYL)-1,3-DIOXOLAN-2-YL]METHOXY]PHENYL]-1-PIPERAZINYL]PHENYL]-2,4-DIHYDRO-2-(1-METHYLPROPYL)-3H-1,2,4-TRIAZOL-3-ONE

Add sodium hydride (120 mg; oil disp.) to a solution of 2,4-dihydro-4-[4-[4-(4-hydroxyphenyl)-1-piperazinyl]-phenyl]-2-(1-methylpropyl)-3H-1,2,3-triazol-3-one (1.0 g) in dry DMF (20 mL). Warm the mixture at 30°–35° C. for ½ hour. Add a solution of (±)cis-1-[[2-(bromomethyl)-4-(2,4-difluorophenyl)-1,3-dioxolan-4-yl]methyl]-1H-1,2,4-triazole prepared in Example 13 (1.2 g) in dry DMF (10 mL) and heat (bath temp. 90° C.) for 3 h. Cool, pour into (200 mL) ice water, extract with EtOAc (2×200 mL) and wash with water (75 mL). Dry the EtOAc extract with $Na_2SO_4$ and evaporate to dryness in vacuo. Chromatograph the residue so obtained on silica gel to provide (1.0 g) product of the title compound, m.p. 158°–161° C.

EXAMPLE 18

(±)CIS-1-ACETYL-4-[4[[4-(2,4-DIFLUOROPHENYL)-4-(1H-1,2,4-TRIAZOL-1-YLMETHYL)-1,3-DIOXOLAN-2-YL]METHOXY]PHENYL]PIPERAZINE

To a stirred solution of 1-acetyl-4-(4-hydroxyphenyl)-piperazine (2.56 g) in dry DMF (30 mL), add sodium hydride (660 mg 60% or disp.). Maintain at room temperature during addition. After 1 hr, add (±)-cis-1-[[2-(bromomethyl)-4-(2,4-difluorophenyl)-1,3-dioxolan-4-yl]methyl]-1H-1,2,4-triazole prepared in Example 17 (3.0 g) dissolved in dry DMF (15 mL) and heat the solution (bath temp. 85° C.) for 2 hr. Remove most of the DMF in vacuo and take up the residue in water (400 mL) extract with EtOAc (2×200 cc) and wash with 10% $K_2CO_3$, then water. Dry the EtOAc extract over $Na_2SO_4$ and evaporate to give a residue. Chromatograph the residue on silica gel to provide the title compound (2.3 g) m.p. 158°–160° C.

EXAMPLE 19

(±)CIS-1-[4-[[4-(2,4-DIFLUOROPHENYL)-4-(1H-1,2,4-TRIAZOL-1-YLMETHYL)-1,3-DIOXOLAN-2-YLMETHOXY]PHENYL]-4-(1-METHYLETHYL)-PIPERAZINE

Add NaH (320 mg, 60% on disp.) to a dispersion of 1-(4-hydroxyphenyl)-4-(1-methylethyl)piperazine (1.7 g) in dry DMF (20 mL) and stir for 1 hr. Add a solution of (±) cis-1-[[2-(bromomethyl)-4-(2,4-difluorophenyl)-1,3-dioxolan-4-yl]methyl]-1H-1,2,4-triazole prepared in Examples 14 (2 g) in dry DMF (10 mL) at room temperature in dry DMF (20 mL) and stir for 1 hr. Add solution of and heat the reaction for 1 hr at 100° C. Cool and remove the DMF in vacuo at 45° C. Dilute the residue with water (100 mL) and extract with EtOAc (2×50 mL). Wash with water, dry over $Na_2SO_4$ and evaporate the organic solvent, to give an oil. Chromatograph the oil on silica gel to give the title compound (610 mg) m.p. 125°–127° C.

EXAMPLE 20

(±)-CIS AND TRANS-DERIVATIVES OF 4-(2,4-DICHLOROPHENYL)-1,3-DIOXOLAN-4-YL]METHYL]-1H-1,2,4-TRIAZOLES OF THE FORMULAS

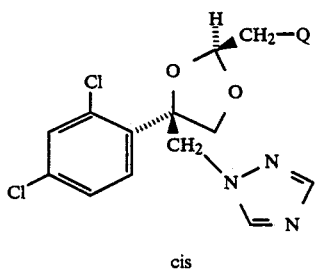

cis

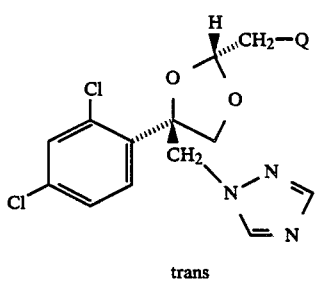

trans (a) Follow the procedure of Example 8 except substitute for 1-(p-hydroxyphenyl)-piperazine-N-acetate equivalent quantities of the compounds listed under HQ

HQ

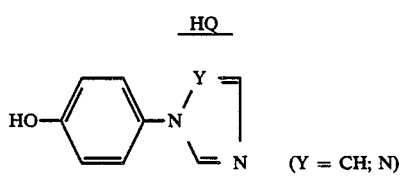

(Y = CH; N)

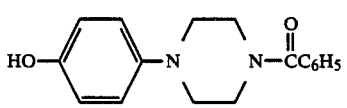

-continued

HQ

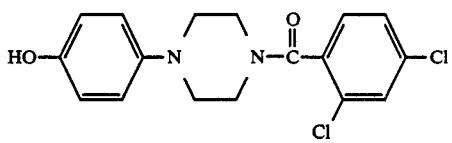

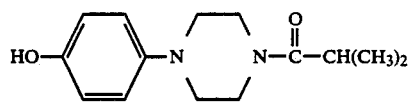

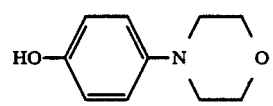

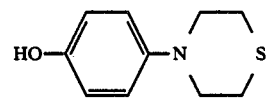

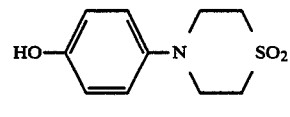

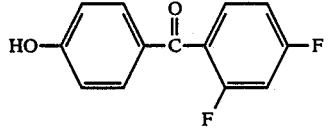

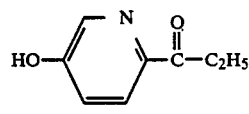

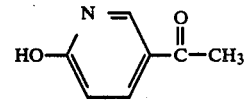

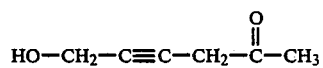

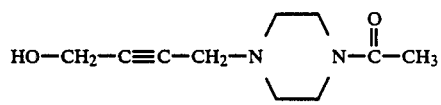

to produce the corresponding (±) cis compounds of above formula with the appropriate Q group.

(b) Follow the procedure of Example 9 except substitute for 1-acetyl-4-(4-hydroxyphenyl)-piperazine equivalent quantities of the compounds of formulas HQ in Example 20(a) to provide the corresponding (±) trans compounds with the appropriate Q group.

EXAMPLE 21

PREPARATION OF (±)CIS AND TRANS-4-(2,4-DIFLUOROPHENYL)-1,3-DIOXOLAN-4-YL]METHYL](1H-1,2,4-TRIAZOLES OF THE FORMULAS

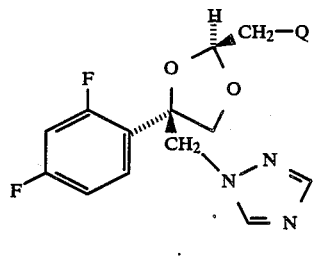
cis

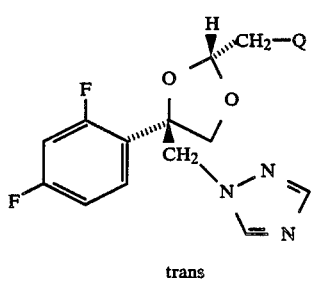
trans (a) Follow the procedure of Example 18 except substitute for 1-acetyl-4-(4-hydroxyphenyl)piperazine equivalent quantities of the following compounds listed under HQ

HQ

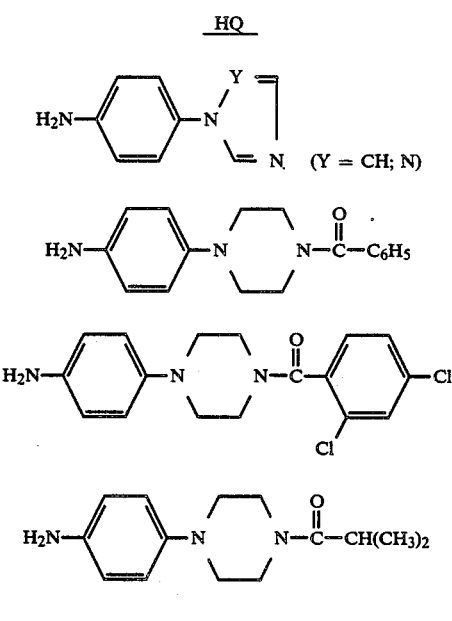

HQ

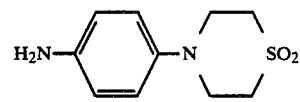

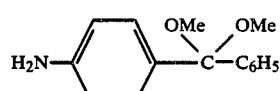

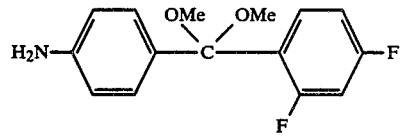

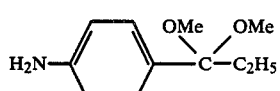

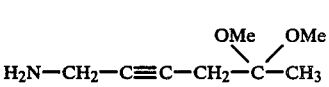

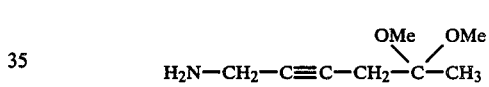

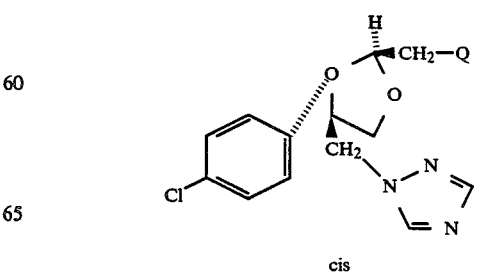

to provide the corresponding (±)-cis compounds of the aboye formula with the appropriate Q group.

(b) Follow the procedure of Example 18 but substitute for the ±cis triazole an equivalent quantity of the (±)trans triazole from Example 7 and for the 1-acetyl-4-(4-hydroxyphenyl)piperazine equivalent quantities of the compounds of formula HQ listed in Example 21 (a) to provide the corresponding (±)trans compounds of the aboye formula with the appropriate Q group.

EXAMPLE 22

(±)-CIS AND (±)-TRANS DERIVATIVES OF 4(4-CHLOROPHENYL)-1,3-DIOXOLAN-4-YL]METHYL]-1H-TRIAZOLES OF THE FORMULAS cis -continued

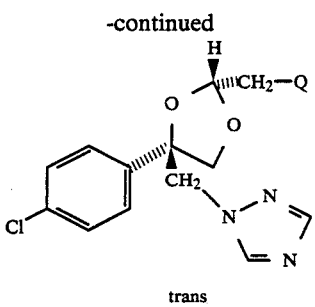
trans (a) Follow the procedure of Example 3 except substitute for 1-(4-hydroxylphenyl-N-acetate) equivalent quantities of the following compounds listed under HQ

HQ

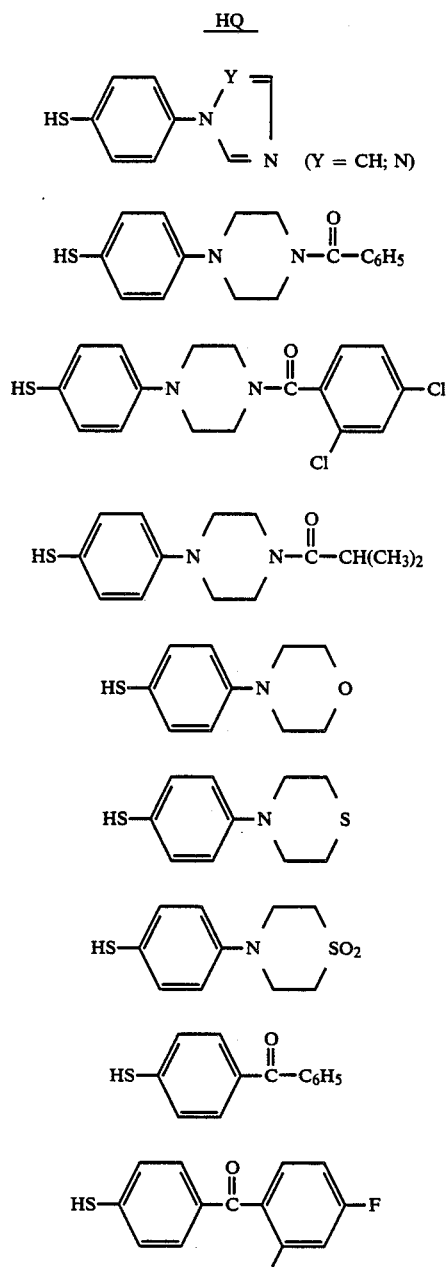

-continued
HQ

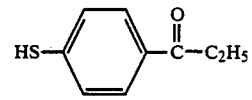

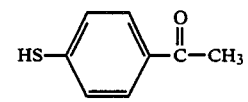

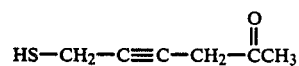

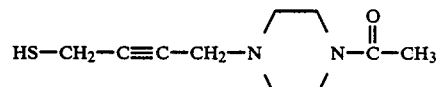

to produce the corresponding ±(cis) compounds of the above formulas with the appropriate Q group.

(b) Follow the procedure of Example 22 except substitute for the (±)cis triazoles, e.g. an equivalent of the (±)1-[[2-(bromomethyl)-4-(4-chlorophenyl)-1,3-dioxolan-4-yl]methyl]-1H-1,2,4-triazole of Example 2 to obtain the corresponding (±)trans compounds of the above formula with the appropriate Q group.

What is claimed is:

1. A compound represented by the formula I:

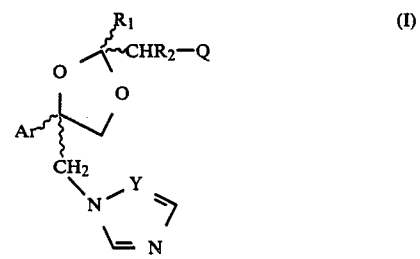

wherein Ar is thienyl, pyridyl, biphenyl, phenyl or phenyl substituted by one or more of halo, nitro, cyano, lower alkyl, lower alkoxy or perhalo(lower)alkyl;

Y is CH or N;

Q is

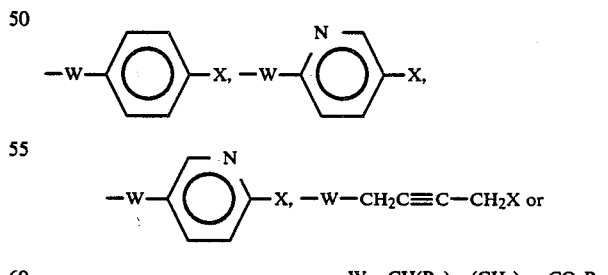

W is $-NR_5-$, $-O-$ or $-S(O)_n-$;

X is $NO_2$, $NR_6R_7$ or $COR_8$;

$R_1$, $R_2$, $R_3$ and $R_4$ are independently hydrogen or lower alkyl; $R_5$ is hydrogen, lower alkyl or ($C_2$-$C_6$)alkanoyl; $R_6$ and $R_7$ are independently hydrogen, lower alkyl, phenyl or phenyl substituted by one or more of halo, perhalo(lower)alkyl, (C$_2$-C$_8$)alkanoyl, lower alkyl, lower alkoxy, or 2-(lower)alkyl-3-oxo-1,2,4-triazol-4-yl, or R$_6$ and R$_7$ taken together with the nitrogen atom in NR$_6$R$_7$ form unsubstituted or substituted five- or six-membered heterocyclic ring systems containing at least one carbon atom and one to four heteroatoms chosen from N, O, S, SO and SO$_2$, said heterocyclyl substituents being (C$_2$-C$_6$)alkanoyl, lower alkyl, phenyl or phenyl substituted by one or more of halo, perhalo, lower alkyl, C$_2$-C$_6$)alkanoyl, lower alkyl, lower alkoxy, or 2-loweralkyl-3-oxo1,2,4-triazol-4-yl; R$_8$ is a lower alkyl, lower alkoxy, —NR$_1$R$_2$, phenyl or phenyl substituted by one or more of halo, perhalo lower alkyl, lower alkoxy, nitro, cyano, (C$_2$-C$_6$)alkanoyl; p is 0, 1, 2, 3, 4 or 5; n is 0, 1 or 2; and the stereochemical isomers thereof in racemic or optically active form; or a pharmaceutically acceptable salt thereof.

2. A compound of claim 1 wherein Q is

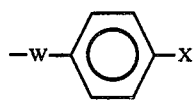

3. A compound of claim 2 wherein X is NR$_6$R$_7$.
4. A compound of claim 3 wherein NR$_6$R$_7$ is

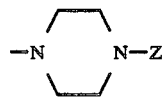

wherein Z is hydrogen, (C$_2$-C$_6$)alkanoyl, lower alkyl, lower alkoxy, perhalo lower alkyl, phenyl or substituted phenyl by one or more of cyano, nitro, halo, perhalo lower alkyl, lower alkoxy, lower alkyl or 2-lower alkyl-3-oxo-1,2,4-triazol-4-yl.

5. A compound of claim 1 wherein Q is

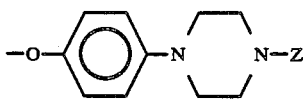

wherein Z is hydrogen, (C$_2$-C$_6$) alkanoyl, lower alkyl, lower alkoxy, perhalo lower alkyl, phenyl or phenyl substituted by one or more of cyano, nitro, halo, perhalo lower alkyl, lower alkyl, lower alkoxy, (C$_2$-C$_6$)alkanoyl or 2-lower alkyl-3-oxo-1,2,4-triazol-4-yl.

6. A compound of claim 1 wherein Q is —S(O)$_n$—CH(R$_3$)—(CH$_2$)$_p$—CO$_2$R$_4$.

7. A compound of claim 1 which is ($\pm$)cis-1-acetyl-4-[4-[[4-(4-chlorophenyl)-4-(1H-1,2,4-triazol-1-ylmethyl)-1,3-dioxolan-2-yl]methoxy]phenyl]piperazine.

8. A compound of claim 1 which is ($\pm$)trans-1-acetyl-4-[4-[[4-(4-chlorophenyl)-4-(1H-1,2,4-triazol-1-ylmethyl)-1,3-dioxolan-2-yl]methoxy]phenyl]piperazine.

9. A compound of claim 1 which is ($\pm$)cis-4-[4-[4-[4-[[4-(2,4-difluorophenyl)-4-(1H-1,2,4-triazol-1-ylmethyl)-1,3-dioxolan-2yl]methoxy]phenyl]-1-piperazinyl]phenyl]-2,4-dihydro-2-(1-methylpropyl)-3H-1,2,4-triazole-3-one.

10. A compound of claim 1 which is ($\pm$)cis-1-[4-[[4-(2,4-difluorophenyl)-4-(1H-1,2,4-triazol-1-ylmethyl)-1,3-dioxolan-2-yl]methoxy]phenyl]-4-(1-methylethyl)piperazine.

11. A compound of claim 1 which is methyl($\pm$)cis-6-[[[4-(2,4-difluorophenyl)-4-(1H-1,2,4-triazol-1-ylmethyl)-1,3-dioxolan-2-yl]methyl]thio]hexanoate.

12. A compound of claim 1 which is ($\pm$)cis-6-[[[4-(2,4-difluorophenyl)-4-(1H-1,2,4-triazol-1-ylmethyl)-1,3-dioxolan-2-yl]methyl]thio]hexanoic acid.

13. A compound of claim 1 which is ($\pm$)cis-1-acetyl-4-[4-[[4-(2,4-dichlorophenyl)-4-(1H-imidazol-1-ylmethyl)-1,3-dioxolan-2-yl]methoxy]phenyl]piperazine.

14. A compound of claim 1 which is ($\pm$)cis-1-acetyl-4-[4-[[4-(2,4-difluorophenyl)-4-(1H-1,2,4-triazol-1-ylmethyl)-1,3-dioxolan-2-yl]methoxy]phenyl]piperazine.

15. A compound of claim 1 which is ($\pm$)trans-1-acetyl-4-[4-[[4-(2,4-dichlorophenyl)-4-(1H-imidazol-1-ylmethyl)-1,3-dioxolan-2-yl]methoxy]phenyl]piperazine.

16. A compound of claim 1 which is ($\pm$)cis-1-acetyl-4-[4-[[4-(2,4-dichlorophenyl)-4-(1H-imidazol-1-ylmethyl)-2-methyl-1,3-dioxolan-2-yl]methoxy]phenyl]piperazine.

17. A composition for treating or preventing an allergic reaction in a host which comprises an antiallergically effective amount of a compound of claim 1 and a pharmaceutically acceptable carrier.

18. A composition for treating or preventing susceptible fungal infection which comprises an antifungally effective amount of a compound of claim 1 and a pharmaceutically acceptable carrier.

19. A method of treating or preventing susceptible fungal infections which comprises administering to a host in need of such treating or preventing an antifungally effective amount of a compound of claim 1 or a pharmaceutical composition comprising such a compound and a pharmaceutically acceptable carrier.

20. A method of treating or preventing an allergic reaction in a host which comprises administering to such a host in need of such treatment or prevention an antiallergically effective amount of a compound of claim 1 or a pharmaceutical composition thereof.

* * * * *